United States Patent [19]

Simonovitch et al.

[11] Patent Number: 4,566,995
[45] Date of Patent: Jan. 28, 1986

[54] PROCESS FOR THE PREPARATION OF BENZOTHIAZEPINE DERIVATIVES

[75] Inventors: Chaim Simonovitch, Rishon Letzion; Theodor Hoffman, Netanya; Sabar Sasson, Rehovoth, all of Israel

[73] Assignee: ABIC Ltd., Israel

[21] Appl. No.: 718,100

[22] Filed: Apr. 1, 1985

[30] Foreign Application Priority Data

Apr. 13, 1984 [IL] Israel ........................................ 71538

[51] Int. Cl.⁴ .......................................... C07D 281/02
[52] U.S. Cl. .............................................. 260/239.3 B
[58] Field of Search ................................. 260/239.3 B

[56] References Cited

U.S. PATENT DOCUMENTS 3,562,257  2/1971  Kugita et al. ................. 260/239.3 B
4,416,819  11/1983 Nagao et al. ................. 260/239.3 B
4,438,035  3/1984  Gaino et al. .................. 260/239.3 B
4,521,430  6/1985  Oh-Ishi et al. ............... 260/239.3 B Primary Examiner—Robert T. Bond
Attorney, Agent, or Firm—Steinberg & Raskin

[57]  ABSTRACT

The present invention relates to a process for the preparation of benzothiazepine derivatives of general formula I

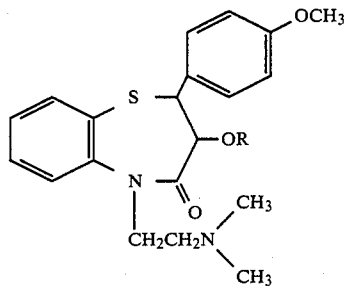

wherein R stands for hydrogen and acetyl or of acid addition salts thereof in which a corresponding compound of general formula II

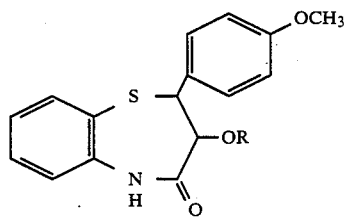

in which R has the same meaning as above is reacted with 2-(dimethylamino)-ethyl chloride in a biphasic system of water and a non-combustible aliphatic polychlorinated hydrocarbon solvent in the presence of calcium hydroxide or of barium hydroxide. The process is advantageously performed at a temperature between 15° and the refluxing temperature of the aliphatic polychlorinated hydrocarbon solvent. The process is optionally performed in the presence of a suitable quaternary ammonium halide. In the process the amount of calcium hydroxide or barium hydroxide is advantageously 1-3 moles per 1 mole of the compound of general formula II, the amount of aliphatic polychlorinated hydrocarbon solvent is advantageously 15-40 ml and that of water 3-10 ml per g of the compound of general formula II and the ratio aliphatic chlorinated hydrocarbon solvent:water is advantageously 2:1 to 10:1.

11 Claims, No Drawings

PROCESS FOR THE PREPARATION OF BENZOTHIAZEPINE DERIVATIVES

The present invention relates to a novel process for the preparation of benzothiazepine derivatives of general formula I

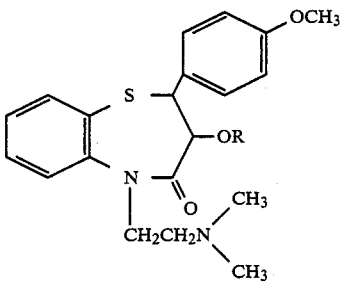

wherein R stands for hydrogen and acetyl; and a pharmaceutically acceptable salt thereof.

The benzothiazepine derivative of general formula I being cis(+)-2-(4'-methoxyphenyl)-3-acetyloxy-5[2-(dimethylamino)ethyl]-2,3 dihydro-1,5-benzothiazepine-4-5(H)one (hereinafter called "diltiazem"), is an effective calcium antagonist. The compound in which R stands for hydrogen serves as intermediate for the preparation of diltiazem.

British patent specification No. 1236467 describes the preparation of a compound of general formula I by converting a corresponding compound of general formula II

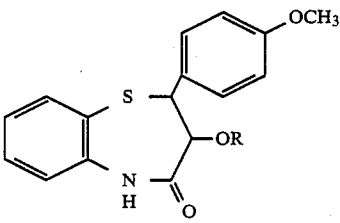

into its alkali metal salt by treating it with an alkali metal, e.g. sodium and potassium; an alkali metal hydride; and an alkali metal amide, in a solvent, e.g. dioxane, toluene, xylene or dimethylsulfoxide; whereafter said alkali metal salt is reacted with a 2-(dimethylamino)-ethyl halide of general formula III

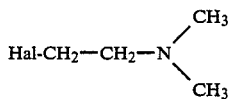

in which Hal stands for a halogen atom.

It is known that working with alkali metals, alkali metal hydrides and alkali metal amides is in most instances dangerous. Moreover, the procedure being mentioned in said British specification as being preferred, namely the use of sodium hydride and of dimethylsulfoxide is considered to be unsafe for industrial use, as explosions have been reported when this system was used.

European patent specification No. 81234 describes the preparation of a compound of general formula I in which R has the same meaning as above in which a corresponding compound of general formula II is reacted with a compound of general formula III in the presence of potassium hydroxide in acetone; or in the presence of potassium carbonate in acetone, in a lower alkyl acetate or in a mixture of one of said solvents with water. The solvents used in this process are highly combustible. Thus, special explosion-proof equipment has to be used and precautions have to be taken for carrying out said process on an industrial scale.

In both of the above processes when the compound of formula II wherein R stands for hydrogen, is treated with a compound of formula II, the product obtained, if desired, is not directly acetylated but is first purified by converting it into its hydrochloride.

From Japanese patent specification No. 58029779 there is known a process for the preparation of a compound of general formula I in which R stands for acetyl in which a compound of general formula II, in which R stands for acetyl, is reacted with a compound of general formula III with a base in an essentially anhydrous organic solvent in the presence of an intraphasal transfer catalyst. The only example given in said specification uses as base potassium hydroxide, as solvent acetonitrile and as catalyst a crown ether. The other bases which are specifically mentioned are other alkaline nemetal hydroxides. The use of an alkali earth metal hydroxide has not been mentioned. The yield given in said specification is unsatisfactory.

Some of the above known processes use solvents which are quite expensive and even toxic. Moreover, in those processes in which the intermediate, i.e. the compound of general formula I in which R stands for hydrogen has to be converted into diltiazem, said intermediate has first to be isoltaed and purified.

The object of the present invention is thus to provide a process for the preparation of compounds of general formula I which overcomes many of the above drawbacks. This process should give good yields, very pure compounds, be safe and economic, not require complicated apparatus, utilise relatively cheap, non-toxic and non-combustible solvents and not require anhydrous conditions and the use of dehydrating agents. Moreover, it should not require the purification of the intermediate when diltiazem has to be prepared.

The present invention thus consists in a process for the preparation of compounds of general formula I or of acid addition salts thereof in which a corresponding compound of general formula II is reacted with 2-(dimethylamino)-ethyl chloride in a biphasic system of water and a non-combustible aliphatic polychlorinated hydrocarbon solvent in the presence of calcium hydroxide or of barium hydroxide.

The compound of general formula I wherein R stands for hydrogen obtained from the reaction can, if desired, be acetylated directly without purification.

The compounds of general formula I are, if desired, converted into their acid-addition salts by reacting same, in a suitable solvent with an appropriate inorganic or organic acid.

The compounds of general formula I obtained by the reaction are isolated by methods known per se.

The reaction is advantageously carried out at temperatures between 15° (all temperatures are given herein in degrees centigrade) and the refluxing temperature of the aliphatic polychlorinated hydrocarbon solvent, preferably between 25° and 70°.

Suitable hydrocarbon solvents are, for example, methylene chloride, chloroform and 1,2-dichloroethane.

The process according to the present invention may be performed, if desired, in the presence of a suitable quarternary ammonium halide, e.g. triethylbenzylammonium chloride, didecyl dimethyl ammonium bromide, etc.

The amount of calcium hydroxide or of barium hydroxide to be used in the process according to the present invention is preferably 1–3 moles, especially 2–2.5 moles, per mole of the compound of general formula II. The amount of aliphatic chlorinated hydrocarbon solvent used is preferably 15–40 ml, especially 15–25 ml per g of said compound of general formula II. THe suitable amount of water is preferably 3–10 ml, especially 4–6 ml, per g of said compound of general formula II. The suitable ratio between said aliphatic chlorinated hydrocarbon and water is preferably 2:1 to 10:1.

Asuitable amount of quarternary ammonium halide, if preseent, is 1–10%, preferably 6–8%, by weight of said compound of general formula II.

When calcium- or barium hydroxide were substituted by ammonia, magnesium hydroxide, potassium hydroxide, sodium hydroxide or potassium carbonate, using the above conditions, unsatisfactory results were obtained.

The compounds of general formula II exist in the form of two stereoisomers and each one exist further in the form of two optical isomers. All of said isomers or mixtures thereof can be used in the present invention to give the corresponding isomer of general formula I.

The process according to the present invention overcomes many of the drawbacks of the known processes. It gives good yields of a product of high purity, is safe and economic, utilises relatively cheap, non-toxic and non-combustible solvents and does not require anhydrous conditions and the use of dehydrating agents. Moreover, the compound of general formula I in which R stands for hydrogen need not be purified but can directly be acetylated to give the compound of general formula I in which R stands for acetyl. Thus, at least one chemical step is saved.

The compounds of general formula II can be prepared by methods known per se, for example, those described in H. Kugita et al., Chem. Pharm. Bull. (Tokyo), 18, 228 & 2028 (1970) and 19, 593 (1971).

The invention will now be illustrated with reference to the following Examples without being limited by them.

EXAMPLE 1

3.43 g of cis-(+)-2-(4′-methoxyphenyl)-3-acetyloxy-2,3-dihydro-1,5-benzothiazepine-4(5H)-one, 3.6 g of 2-(dimethylamino)-ethyl chloride-hydrochloride and 1.87 g of calcium hydroxide were added to 60 ml of methylene chloride and 10 ml of water. The mixture obtained was stirred vigorously at the interphase and 0.2 g of triethylbenzylammonium chloride were added. The reaction mixture was then heated to 50° and stirring was continued at that temperature for 24 hours. After cooling the organic phase was separated, washed once with water, dried over anhydrous sodium sulfate, filtered and evaporated to dryness. 75 ml of isopropyl alcohol and 2 ml of 25% hydrogen chloride in isopropanol were added to the crude diltiazem base obtained and the mixture was cooled to 0°. 3.2 g of diltiazem were filtered off. M.p. 211°–215°; $[\alpha]_D + 112$ (C=1, $H_2O$).

EXAMPLE 2

3.43 g of cis-(+)-2-(4′-methoxyphenyl)-3-acetyloxy-2,3-dihydro-1,5-benzothiazepine-4(5H)-one, 3.6 g of 2-(dimethylamino)-ethyl chloride-hydrochloride and 6.38 g of barium hydroxide were added to 60 ml of methylene chloride and 10 ml of water. The mixture obtained was stirred vigorously at the interphase and 0.2 g of triethylbenzylammonium chloride were added. The reaction mixture was then heated to 40° and stirring was continued at that temperature for 24 hours. After cooling the organic phase was separated, washed once with water, dried over anhydrous sodium sulfate, filtered and the solvent was then removed by rotary evaporation. 75 ml of isopropyl alcohol and 2 ml of 25% hydrogen chloride in isopropanol were added to the crude diltiazem base thus obtained and the mixture was then cooled to 0°. 3,3 g of diltiazem hydrochloride were filtered off. M.p. 211°–215°; $[\alpha]_D + 114$ (C=1, $H_2O$).

EXAMPLE 3

7.4 g of crude cis-(+)-2-(4′-methoxyphenyl)-3-hydroxy-5-(2′-dimethylamino-ethyl)-2,3-dihydro-1,5-benzothiazepine-4(5H)-one were added to 4.08 g of acetic anhydride in 35 ml of dry toluene. The mixture was heated to reflux for 3 hours. The mixture was then cooled to 40° with stirring and 12 ml of water were then added. 7 g of sodium bicarbonate were added portionwise in the coarse of 2–3 hours to pH 7.5. The organic phase was separated, washed with a small amount of water and then dried by means of azeotropic distillation. The residue was cooled to 5° and then 0.8 g of hydrogen chlorine in 4 ml of isopropyl alcohol were added and stirring was continued at 0°–5° for 2 hours. The crystals obtained were filtered off, washed twice with 5 ml of cold toluene and dried under vacuum to give 8.3 g of crude diltiazem hydrochloride. A single recrystallisation from 200 ml of isopropanol gave 7.95 g of diltiazem hydrochloride; m.p. 215°. After concentration of the mother liquor and additional 0.25 g of pure diltiazem hydrochloride were recovered.

EXAMPLE 4

3 g of cis-(+)-2-(4′-methoxyphenyl)-3-hydroxy-2,3-dihydro-1,5-benzothiazepine-4(5H)-one, 6.4 g of barium hydroxide octahydrate and 0.2 g of triethylbenzylammonium chloride were added under vigorous mechanical stirring to 60 ml of methylene chloride and 10 ml of water. A solution of 3.2 g of 2-(dimethylamino)-ethyl chloride-hydrochloride in 5 ml of water was added to the above mixture during 5 minutes. Stirring was continued for 1 hour at room temperature and then for 6 hours at 40°. After cooling to room temperature the aqueous phase was separated and discarded and the methylene chloride was then removed under vacuum.

The crude cis-(+)-2-(4′-methoxyphenyl)-3-hydroxy-5-(2′-dimethylaminoethyl)-2,3-dihydro-1,5-benzothiazepine-4(5H)-one obtained was dissolved in 50 ml of toluene and then extracted with 50 ml of 1% hydrochloric acid. The acidic extract was made basic with an excess of sodium bicarbonate and then extracted with 50 ml of toluene. The organic layer was then separated and dried by azeotropic distillation using a Dean Stark apparatus. 1.85 g of acetic acid anhydride were added to the dried organic layer and the resulting mixture was treated as described in Example 3 to yield 3.97 g of diltiazem hydrochloride.

EXAMPLE 5

0.2 g of triethylbenzylammonium chloride, 3 g of cis-(+)-2-(4'-methoxyphenyl)-3-hydroxy-2,3-dihydro-1,5-benzothiazepine-4(5H)-one, 1.5 g of calcium hydroxide and 3.2 g of 2-(dimethylamino)-ethyl chloride-hydrochloride in 5 ml of water were added to 60 ml of methylene chloride and 10 ml of water under vigorous mechanical stirring. The mixture obtained was stirred overnight at room temperature and then for 24 hours at 40°. After cooling to room temperature, the aqueous phase was separated and discarded and the methylene chloride was removed under vacuum.

The crude cis-+)-2-(4'-methoxyphenyl)-3-hydroxy-5-(2'-dimethylaminoethyl)-2,3-dihydro-1,5-benzothiazepine-4(5H)-one obtained was dissolved in 50 ml of toluene and then extracted with 50 ml of 2% hydrochloric acid. The acidic extract was treated with an excess of sodium bicarbonate and then extracted with 50 ml of toluene. The organic layer was then separated and dried by azeotropic distillation using a Dean Stark apparatus.

1.85 g of acetic acid anhydride were added to the dried organic layer and the resulting mixture was treated as described in Example 3 to yield 3.88 g of diltiazem hydrochloride.

EXAMPLE 6

0.2 g of triethylbenzylammonium chloride, 3 g of cis-(+)-2-(4'-methoxyphenyl)-3-hydroxy-2,3-dihydro-1,5-benzothiazepine-4(5H)-one and 6.4 g of barium hydroxide octahydrate were added under vigorous stirring to 60 ml of methylene chloride and 10 ml of water. A solution of 3.2 g of 2-(dimethylamino)-ethyl chloride-hydrochloride in 5 ml of water was added dropwise to the above mixture during 5 minutes. Stirring was continued at room temperature for 1 hour and then at 40° for 24 hours. After cooling to room temperature the aqueous phase was separated and discarded and the methylene chloride was removed under vacuum. (Petroleum ether (40°-60°) was added to the viscous residue with induced crystallisation. The crystals obtained were filtered off and dried under vacuum to yield 3.7 g of cis-(+)-2-(4'-methoxyphenyl)-3-hydroxy-5-(2'-dimethylaminoethyl)-2,3-dihydro-1,5-benzothiazepine-4(5H)-one; m.p. 88°–90°; $[\alpha]_D^{27} + 169$ (C=0.25, CH$_3$OH).

EXAMPLE 7

3 g of cis-(+)-2-(4'-methoxyphenyl)-3-hydroxy-2,3-dihydro-1,5-benzothiazepine-4(5H)-one and 6.4 g of barium hydroxide octahydrate were added with vigorous stirring to 60 ml of chloroform and 10 ml of water. A solution of 3.2 g of 2-(dimethylamino)-ethyl chloride-hydrochloride in 5 ml of water was added dropwise to the above mixture in the course of 5 minutes. Stirring was continued for 24 hours at room temperature and then for 8 hours at 40°. After cooling to room temperature the aqueous phase was separated and discarded and the chloroform was removed under vacuum. Petroleum-ether (40°-60°) was added to the viscous residue which induced crystallisation. The precipitated crystals were filtered off and dried under vacuum to yield 3.63 g of cis-(+)-2-(4'-methoxyphenyl)-3-hydroxy-5-(2'-dimethylaminoethyl)-2,3-dihydro-1,5-benzothiazepine-4(5H)-one; m.p. 88°; $[\alpha]_D^{22} + 169$ (C=0.25 CH$_3$OH).

EXAMPLE 8

0.4 g of triethylbenzylammonium chloride, 6 g of cis-(+)-2-(4'-methoxyphenyl)-3-hydroxy-2,3-dihydro-1,5-benzothiazepine-4(5H)-one and 14.8 g of barium hydroxide octahydrate were added under vigorous stirring to 120 ml of chloroform and 14 ml of water. A solution of 6.4 g of 2-(dimethylamino)-ethyl chloride-hydrochloride in 10 ml of water was added dropwise to the above mixture in the course of 5 minutes. Stirring was continued for 17 hours at room temperature and then for 2 hours at 60°. After cooling to room temperature unreacted barium hydroxide octahydrate was filtered off, the aqueous phase was separated and discarded and the chloroform was removed under vacuum.

The crude cis-(+)-2-(4'-methoxyphenyl)-3-hydroxy-5-(2'-dimethylaminoethyl)-2,3-dihydro-1,5-benzothiazepine-4(5H)-one obtained was dissolved in 50 ml of toluene and then extracted with 100 ml of 2.8% hydrochloric acid. The acidic extract was treated with an excess of sodium bicarbonate and then extracted with 100 ml of toluene. The organic layer was separated and dried by azeotropic distillation using a Dean Stark apparatus. 4 g of acetic acid anhydride were added to the dried organic layer and the resulting mixture was treated as described in Example 3 to yield 7.6 g of diltiazem hydrochloride; m.p. 212°; $[\alpha]_D^{20} = 117.97$ (c=1, H$_2$O).

EXAMPLE 9

6 g of cis-(+)-2-(4'-methoxyphenyl)-3-hydroxy-2,3-dihydro-1,5-benzothiazepine-4(5H)-one and 6.4 g of barium hydroxide octahydrate were added under vigorous mechanical stirring to 120 ml of 1,2-dichloroethane and 14 ml of water. A solution of 6.4 g of 2-(dimethylamino)ethyl chloride-hydrochloride in 10 ml of water was added dropwise to the above mixture in the course of 5 minutes. Stirring was continued at room temperature for 1 hour and then for 1.5 hours at 70°. After cooling to room temperature the unreacted barium hydroxide octahydrate was filtered off, the aqueous phase was separated and discarded and the 1,2-dichlororethane was removed under vacuum.

The crude cis-(+)-2-(4'-methoxyphenyl)-3-hydroxy-5-(2'-dimethylaminoethyl)-2,3-dihydro-1,5-benzothiazepine-4(5H)-one was dissolved in 50 ml of toluene and then treated with an excess of sodium bicarbonate and then extracted with 100 ml of toluene. The organic layer was separated and dried by azeotropic distillation using a Dean Stark apparatus. 3.7 g of acetic acid anhydride were added and the resulting mixture was treated as described in Example 3 to yield 6.94 g of diltiazem hydrochloride; m.p. 211°–213°.

EXAMPLE 10

0.2 g of triethylbenzylammonium chloride, 3 g of trans-(+)-2-(4'-methoxyphenyl)-3-hydroxy-2,3-dihydro-1,5-benzothiazepine-4(5H)-one and 6.4 g of barium octahydrate were added under vigorous stirring to 60 ml of 1,2-dichloroethane and 7 ml of water. A solution of 3.2 g of 2-(dimethylamino)-ethyl chloride-hydrochloride in 5 ml of water was added dropwise to the above mixture during 5 minutes. Stirring was continued at room temperature for 1 hour and then for 1.5 hours at 70°. After cooling to room temperature the aqueous phase was separated and discarded and the 1,2-dichloroethane was removed under vacuum. The residue was dissolved in 50 ml of toluene and then extracted with 50 ml of 3% HCl. The acidic extract was treated with an excess of a sodium bicarbonate solution and then extracted with 50 ml of toluene. The toluene was removed under vacuum to yield 3.5 g of trans (+)-2-(4'methoxyphenyl)-3-hydroxy-5-(2'-dimethylaminoethyl)-2,3-dihydro-1,5-benzothiazepine-4(5H)-one; m.p. 115°–117°.

We claim:

1. A process for the preparation of benzothiazepine derivatives of general formula I

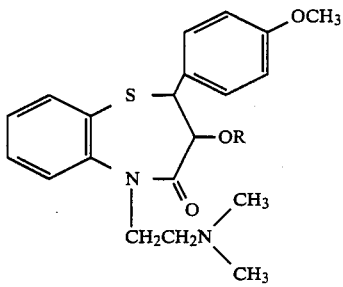

wherein R stands for hydrogen and acetyl or of acid addition salts thereof in which a corresponding compound of general formula II

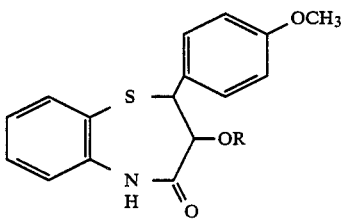

in which R has the same meaning as above is reacted with 2-(dimethylamino)-ethyl chloride in a biphasic system of water and a non-combustible aliphatic polychlorinated hydrocarbon solvent in the presence of calcium hydroxide or of barium hydroxide.

2. A process according to claim 1, in which the compound of general formula I is converted into the acid addition salt by reacting said compound in a suitable solvent with an appropriate inorganic or organic acid.

3. A process according to claim 1, wherein the compound of general formula I in which R stands for hydrogen is acetylated directly without purification.

4. A process according to claim 1, wherein the reaction is performed at temperatures between 15° and the refluxing temperature of the aliphatic polychlorinated hydrocarbon solvent, preferably between 25° and 70°.

5. A process according to claim 1 wherein the aliphatic polychlorinated hydrocarbon solvent is selected among the group comprising methylene chloride, chloroform and 1,2-dichloroethane.

6. A process according to claim 1, wherein the reaction is performed in the presence of a suitable quaternary ammonium halide, preferably selected among the group comprising triethylbenzylammonium chloride and didecyl dimethyl ammonium bromide.

7. A process according to claim 1, wherein the amount of calcium hydroxide or barium hydroxide used is 1–3 moles per mole of the compound of general formula II, preferably 2–2.5 moles per mole.

8. A process according to claim 1, wherein the amount of aliphatic polychlorinated hydrocarbon solvent used is 15–40 ml per g of the compound of general formula II, preferably 15–25 ml per g.

9. A process according to claim 1, wherein the amount of water used is 3–10 ml per g of the compound of general formula II, preferably 4–6 ml per g.

10. A process according to claim 1, wherein the ratio aliphatic chlorinated hydrocarbon solvent:water is 2:1 to 10:1.

11. A process according to claim 6, wherein the amount of quaternary ammonium halide present is 1–10% by weight of the compound of general formula II, preferably 6–8%.

* * * * *